(12) United States Patent
Xu et al.

(10) Patent No.: US 6,429,340 B1
(45) Date of Patent: Aug. 6, 2002

(54) PROCESS FOR PRODUCING 2,4,5,-TRIALKYLBENZALDENHYDES

(75) Inventors: Bo-Qing Xu, Beijing (CN); Yasuo Ohnoki, Osaka; Tsukasa Takahashi, Hyogo, both of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/963,421

(22) Filed: Sep. 27, 2001

(30) Foreign Application Priority Data

Sep. 28, 2000 (JP) ........................................ 2000-297105

(51) Int. Cl.⁷ .............................................. C07C 45/49
(52) U.S. Cl. ........................................ 568/428; 568/437
(58) Field of Search ................................. 568/428, 437

(56) References Cited

U.S. PATENT DOCUMENTS 5,910,613 A    6/1999   Schiraldi et al. ............ 568/428
6,303,827 B1 * 10/2001  Saleh et al. .................. 568/428

FOREIGN PATENT DOCUMENTS

JP    6-21093     9/1987
JP    64-75442    3/1989
WO    WO 00/15593    3/2000
WO    WO 00/15594    3/2000

OTHER PUBLICATIONS

J. Org. Chem. 1985, 50, pp. 1483–1486, "Superacid–Catalyzed Formylation of Aromatics with Carbon Monoxide".
Catalysts for production of trimellitic anhydride and pyromellitic dianhydride (Kagaku Kogaku 1986, 50(9), 614–18), Abstract.
Journal of Chem.Sty–Perkin Trans. 1 (1980) No. 1, London Formylation and Acylation Reactions Catalysed by rlfluoromethane sulphonic Acid, pp. 181–186 XP–002187353.
J. Org. Chem. 1995, 60, 3846–3850 "Dual Reactivity of the Formyl Cation as an Electrophile and a Bronsted Acid in Superacids".

* cited by examiner

Primary Examiner—Sreeni Padmanabhan
(74) Attorney, Agent, or Firm—Sughrue Mion PLLC

(57) ABSTRACT

It is an object of the present invention to provide a production method of 2,4,5-trialkylbenzaldehyde from 1,2,4-tribenzaldehyde at low cost and safely.

The present invention provides a production method of a 2,4,5-trialkylbenzaldehyde which comprises carbonylating a 1,2,4-trialkylbenzene with carbon monoxide in the presence of a catalyst, said catalyst comprising trifluoromethanesulfonic acid.

4 Claims, No Drawings

PROCESS FOR PRODUCING 2,4,5,-TRIALKYLBENZALDENHYDES

TECHNICAL FIELD

The present invention relates to a production method of 2,4,5-trialkylbenzaldehydes. More particularly, the invention relates to the production method of a 2,4,5-trialkylbenzaldehyde of value as an intermediate of various chemical products, particularly as a starting material for pyromellitic anhydride.

BACKGROUND ART

Aromatic aldehydes are compounds of great use as intermediates of various chemical products, and trialkylbenzaldehydes, in particular, are intermediates of great industrial importance as precursors of aromatic polycarboxylic acids. Especially 2,4,5-trialkylbenzaldehydes are very important compounds as starting materials of pyromellitic anhydride, the importance of which is steadily increasing in recent years as heat-resistant resins, plasticizers, and epoxy resin curing agents.

The known production method for a trialkylbenzaldehyde includes the method which comprises the liquid-phase oxidation of a tetraalkylbenzene and the carbonylation reaction of a trialkylbenzene with carbon monoxide.

Among these, the carbonylation reaction of a trialkylbenzene with carbon monoxide insures a good yield and may be regarded as an industrially preferred method. However, the known processes involve high reaction pressures and, hence, high equipment costs. Moreover, a catalyst must be used in a large excess over the reactant starting material, thus leaving room for improvement from industrial points of view. It is also known that trimethylbenzaldehyde can be produced from a trialkylbenzene by using an $HF$-$BF_3$ system as the catalyst in a small amount and conducting the reaction at low temperature and low pressure. In this connection, Komatsu in Chemical Engineering, 50[9] (1986) at pages 614–618 discloses the use of $HF$-$BF_3$ as the catalyst in the reaction between pseudocumene(1,2,4-trimethylbenzene) and carbon monoxide relating to the synthesis process for a production of an aromatic aldehyde. However, the catalyst components $HF$ and $BF_3$ are not only highly toxic and corrosive but also gaseous at atmospheric temperature, thus calling for meticulous care in handling.

Meanwhile, in the production of a 2,4,5-trialkylbenzaldehyde for use as a starting material for pyromellitic anhydride, the substituting positions of the three alkyl groups of a starting material trialkylbenzene is necessary be 1-, 2- and 4-positions and additionally selective carbonylation reaction is necessarily effected on the 5-position. Thus, the 5-position of the 1,2,4-trialkylbenzene is necessarily selectively carbonylated and if other positions are carbonylated to give 2,3,5-trimethylbenzaldehyde and 2,3,6-trimethylbenzaldehyde in large amounts, the yield of the object compound is lowered. Furthermore, when a disproportionation reaction of the 1,2,4-trialkylbenzene takes place as described in Examples 17 to 19 of the pamphlet (2000) of WO 00/15594, still more kinds of byproducts are formed to depress the yield. Therefore, a need exists for a technology by which the 5-position of a 1,2,4-trialkylbenzene can be carbonylated with high selectivity and without causing disproportionation reaction.

J. Org. Chem. 50[9] (1985) at page 1483 discloses a carbonylation technology using a 1,3,5-trialkylbenzene as the substrate and $CF_3SO_3H$ as the peracid catalyst. However, there is no description concerning 1,2,4-trialkylbenzenes and the technology has room for further improvement for producing a 2,4,5-trialkylbenzaldehyde with efficiency.

The pamphlet (2000) of WO 00/15593 relating to the method for reacting an alkyl aromatic compound with carbon monoxide in the presence of a carbonylation catalyst with high-boiling point to obtain an alkyl aromatic aldehyde discloses a perfluoroalkylsulfonic acid of 2 to 18 carbon atoms as the carbonylation catalyst with high-boiling point and the pamphlet (2000) of WO 00/15594 discloses a method comprising reacting an alkyl aromatic compound with carbon monoxide in the presence of an acid ionic liquid to obtain an alkyl aromatic aldehyde. Moreover, Japanese Kokai Publication Sho-64-75442 discloses a production method of an aromatic aldehyde which comprises reacting an aromatic compound with carbon monoxide in a super-strong acid in the presence of a copper (I) or silver carbonyl catalyst and Japanese Kokoku Publication Hei-6-21093 discloses a production method of an aromatic aldehyde which comprises reacting an aromatic compound with carbon monoxide in a defined super-strong acid, such as fluorosulfuric acid-antimony pentafluoride, in the presence of a copper (I) or silver carbonyl catalyst.

However, these technologies have room for improvement for the low-cost and safe production of a 2,4,5-trialkylbenzaldehyde through highly selective carbonylation reaction on the 5-position of the 1,2,4-trialkylbenzene.

SUMMARY OF THE INVENTION

Having been developed in the light of the above state of the art, the present invention has for its object to provide a production method of a 2,4,5-trialkylbenzaldehyde from a 1,2,4-trialkylbenzene at low cost and safely.

In the course of their investigation into the various production methods of trialkylbenzaldehydes, the inventors of the present invention paid attention, in the first place, to the carbonylation reaction of a trialkylbenzene with carbon monoxide. In this type of technology, for example, for the purpose of obtaining a starting material for pyromellitic anhydride, the position selectivity of carbonylation is important, that is to say it is necessary that the 5-position of the 1,2,4-trialkylbenzene be selectively carbonylated. If other positions are carbonylated to give 2,3,5-trimethylbenzaldehyde and 2,3,6-trimethylbenzaldehyde in substantial amounts, the yield of the objective compound will be lowered to frustrate the endeavor. However, the inventor found that when a catalyst which comprises trifluoromethanesulfonic acid is used, the 5-position of a 1,2,4-trialkylbenzene is carbonylated with extremely high selectivity to give a 2,4,5-trialkylbenzaldehyde, thus neatly solving the above problems. The finding has resulted in the present invention.

The present invention, therefore, provides a production method of a 2,4,5-trialkylbenzaldehyde which comprises carbonylating a 1,2,4-trialkylbenzene with carbon monoxide in the presence of a catalyst, said catalyst comprising trifluoromethanesulfonic acid.

In the following, the present invention is described in detail.

DETAILED DESCRIPTION OF THE INVENTION

The production method of a 2,4,5-trialkylbenzaldehyde according to the invention includes a step of carbonylating a 1,2,4-trialkylbenzene with carbon monoxide in the presence of a catalyst. In this step, the 2,4,5-trialkylbenzaldehyde is produced by using the 1,2,4-trialkylbenzene as a starting material. The above starting material may or may not contain compounds other than the 1,2,4-trialkylbenzene but preferably the 1,2,4-trialkylbenzene alone is subjected to the production of the 2,4,5-trialkylbenzaldehyde. In this connection, the 1,2,4-trialkylbenzene may be used one species or two or more species.

The alkyl groups of said 1,2,4-trialkylbenzene are not particularly restricted but when the obtained 2,4,5-trialkylbenzaldehyde is to be used as a starting material for pyromellic anhydride, the number of carbon atoms constituting each alkyl group is desirably small, preferably within the range of 1 to 3 carbon atoms. Thus, for example, a methyl, ethyl, propyl and isopropyl group may be mentioned. Three alkyl groups of the 1,2,4-trialkylbenzene may be the same or different.

In the production method according to the invention, the above-mentioned catalyst comprises trifluoromethanesulfonic acid. The catalyst used in the present invention may or may not contain one or more species of compounds other than trifluoromethanesulfonic acid.

The mode of use of trifluoromethanesulfonic acid to be used as said catalyst is not particularly restricted but may be used as it is or as immobilized, for example, by supporting it on a carrier. Immobilization of a catalyst provides for industrial advantages, for example by facilitating separation of the catalyst from the reaction mixture. The carrier is not particularly restricted but includes oxides, carbides or nitrides of metals such as silicon, aluminum, titanium, zirconium, cerium, tin, tungsten, niobium, etc., mixtures thereof, inorganic compounds such as zeolite, silica-alumina, titania-silica, alkali metal salts of heteropoly acids, etc., and organic compounds such as ion exchange resins and porous polymers. These may be used each independently or in a combination of two or more species.

The reaction conditions of the carbonylation reaction according to the present invention are not particularly restricted, but for example, there action is preferably conducted in the presence of 1 to 10 molar equivalents of trifluoromethanesulfonic acid based on the 1,2,4-trialkylbenzene at a carbonmonoxide pressure (CO partial pressure) of 0.01 to 10 MPa and a reaction temperature of −50 to 50° C. The amount of the catalyst affects the conversion rate and reaction rate of the 1,2,4-trialkylbenzene but when trifluoromethanesulfonic acid is used in an amount of 6 molar equivalents based on the 1,2,4-trialkylbenzene, a yield of 93 mole % can be attained. If more than 10 molar equivalents of the catalyst is used, no further improvement will be obtained in the desired effect. The CO partial pressure also affects the reaction rate and conversion rate. If it is not more than 0.1 MPa, the conversion rate may possibly be very low but if it is more than this, the reaction rate and conversion rate will be improved. Increasing the CO partial pressure beyond 10 MPa has no problem on the reaction but an equipment may possibly be expensive. Increasing the reaction temperature improves the reaction rate but, at the same time, encourages the formation of byproducts. The more preferred use amount of trifluoromethanesulfonic acid is 2 to 8 molar equivalents based on the 1,2,4-trialkylbenzene. The more preferred CO partial pressure is 0.2 to 10 MPa and the more preferred reaction temperature is −20 to 30° C.

Referring, further, to reaction conditions, it is effective to enhance the efficiency of contact between CO gas and the reaction mixture containing the reactant starting material, catalyst and so forth, by increasing the agitation speed, for example. In industrial application, it is preferable to take all these factors into consideration and select the economically optimum reaction parameter settings. For example, it is effective to carry out the reaction at a low conversion rate by reducing the amount of the catalyst and the CO partial pressure so as to reduce the cost for the catalyst or construction of the equipment. Conversely, it may be effective in some cases to increase the amount of the catalyst, CO partial pressure and reaction temperature resulting in plant down-sizing. For example, it is obvious that the reaction parameter settings of 4 molar equivalents of trifluoromethanesulfonic acid based on the 1,2,4-trialkylbenzene and a CO partial pressure of as low as about 1 MPa result in a poor yield of the 2,4, 5-trialkylbenzaldehyde as compared with the settings of not less than 6 molar equivalents of trifluoromethanesulfonic acid based on the 1,2,4-trialkylbenzene and a CO partial pressure of not less than 6 MPa, but there may be cases in which the former conditions are favored from the standpoint of catalyst recovery costs and equipment costs.

The method of separating the 2,4,5-trialkylbenzaldehyde produced by said carbonylation reaction from the catalyst is not particularly restricted but can be applied the method in which the reaction mixture after completion of the reaction is directly subjected to a distillation to recover the catalyst by utilizing the difference in boiling point between the catalyst and the product and the method which comprises adding water to the reaction mixture and subjecting it to a solvent extraction so as to recover the catalyst in the aqueous phase and the product in the organic phase. Moreover, when the immobilized catalyst is used, the product and the catalyst can be separated from each other by a known technique such as filtration.

In the production method according to the present invention, 2,4,5-trialkylbenzaldehyde can be produced at low cost and safely by using trifluoromethanesulfonic acid as the catalyst for the carbonylation of 1,2,4-trialkylbenzene with carbon monoxide. The 2,4,5-trialkylbenzaldehyde produced in accordance with the present invention is a compound of great use as an intermediate of chemical products, such as a precursor of aromatic polycarboxylic acids, as well as heat-resistant resins, plasticizers, epoxy resin curing agents and so forth. It is particularly of value as a starting material for pyromellitic anhydride.

In accordance with the present invention, constituted as above, 2,4,5-trialkylbenzaldehydes of value as intermediates of chemical products, such as precursors of aromatic polycarboxylic acids, as well as heat-resistant resins, plasticizers, and epoxy resin curing agents, particularly as starting materials for pyromellitic anhydride can be produced at low cost and safely.

BEST MODE FOR CARRYING OUT THE INVENTION

The following examples illustrate the present invention in further detail without defining the scope of the invention.

EXAMPLE 1

A 100-ml autoclave was charged with 6.7 g of 1,2,4-trimethylbenzene, and 50 g of trifluoromethanesulfonic acid was gradually added. After CO purging, the reaction was conducted at a CO partial pressure of 5 MPa and a reaction temperature of 0° C. for 90 minutes. After completion of the reaction, the reaction mixture was poured in ice-water and the product was extracted into ethyl ether. The ethereal solution thus obtained was analyzed by gas chromatography. The analysis revealed the formation of 2,4,5-trimethylbenzaldehyde in a yield of 93 mole %. The selectivity for 2,4,5-trimethylbenzaldehyde relative to converted 1,2,4-trimethylbenzene was 98%.

From GC and NMR analyses results, neither position isomers nor byproducts attributable to a disproportionation reaction were detected. While two trace byproduct peaks were noted, mass spectrometric analysis revealed that these are high molecular substances approximating the dimer and trimer and could be easily separated from the objective product.

EXAMPLES 2 to 11

The reaction temperature, the ratio of trifluoromethanesulfonic acid to 1,2,4-trimethylbenzene, CO pressure, reaction time and agitation speed were respectively varied as shown in Table 1 and the reaction of Example 1 was otherwise carried out. The results are shown in Table 1.

The values in Table 1 were calculated by means of the following computation formulas.

Catalyst/substrate=[amount of 1,2,4-trifluoromethanesulfonic acid fed (in moles)]/[amount of 1,2,4-trimethylbenzene fed (in moles)]

Conversion=[amount of 1,2,4-trimethylbenzene which reacted (in moles)]/[amount of 1,2,4-trimethylbenzene fed (in moles)]×100

Yield=[amount of 2,4,5-trimethylbenzaldehyde produced (in moles)]/[amount of 1,2,4-trimethylbenzene fed (in moles)]×100.

Selectivity=[amount of 2,4,5-trimethylbenzaldehyde produced (in moles)]/[amount of 1,2,4-trimethylbenzene which reacted (in moles)]×100.

TABLE 1

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| CO pressure (MPa) | 6 | 6 | 6 | 0.1 | 0.2 | 2 | 7.5 | 6 | 6 | 6 | 2 |
| Catalyst/substrate (mole/mole) | 6 | 4 | 2 | 4 | 4 | 4 | 4 | 4 | 4 | 4 | 4 |
| Reaction temperature (° C.) | 0 | 0 | 0 | 0 | 0 | 0 | 0 | 10 | 0 | 0 | 0 |
| Reaction time (min.) | 90 | 90 | 90 | 90 | 90 | 90 | 90 | 90 | 90 | 180 | 360 |
| Agitation speed (rpm) | 360 | 360 | 360 | 360 | 360 | 360 | 360 | 360 | 640 | 360 | 640 |
| Conversion (%) | 94.8 | 72.9 | 17.1 | 2.2 | 42.3 | 69.9 | 75.2 | 77.2 | 76.0 | 80.4 | 80.0 |
| Yield (mole %) | 92.9 | 69.4 | 14.8 | 0.4 | 35.9 | 66.7 | 71.9 | 71.0 | 74.2 | 77.4 | 72.8 |
| Selectivity (mole %) | 98.0 | 95.1 | 86.0 | 17.8 | 85.0 | 95.4 | 95.5 | 92.0 | 97.7 | 96.3 | 91.0 |

What is claimed is:

1. A production method of a 2,4,5-trialkylbenzaldehyde which comprises
    carbonylating of a 1,2,4-trialkylbenzene with carbon monoxide in the presence of a catalyst,
    said catalyst comprising trifluoromethanesulfonic acid
    wherein the 5-position of said 1,2,4-trialkylbenzene is carbonylated with higher selectivity than the other positions.

2. The production method of a 2,4,5-trialkylbenzaldehyde according to claim 1,
    wherein the reaction is conducted in the presence of 1 to 10 molar equivalents of trifluoromethanesulfonic acid based on the 1,2,4-trialkylbenzene at a carbon monoxide pressure of 0.01 to 10 MPa and a reaction temperature of −50 to 50° C.

3. The production method of a 2,4,5-trialkylbenzaldehyde according to claim 2, wherein the carbon monoxide pressure is 0.2 to 10 MPa.

4. The production method of a 2,4,5-trialkylbenzaldehyde according to claim 1, wherein the 2,4,5-trialkylbenzaldehyde is used as a starting material for pyromellitic anhydride.

* * * * *

UNITED STATES PATENT AND TRADEMARK OFFICE
CERTIFICATE OF CORRECTION

PATENT NO.    : 6,429,340 B1
DATED         : August 6, 2002
INVENTOR(S)   : Bo-Qing Xu, Yasuo Ohnoki and Tsukasa Takahashi It is certified that error appears in the above-identified patent and that said Letters Patent is hereby corrected as shown below:

Title page,
Please correct title of invention from: "[54] PROCESS FOR PRODUCING 2,4,5,"
to -- [54] PROCESS FOR PRODUCING 2,4,5-TRIALKYLBENZALDEHYDES --

Signed and Sealed this

Twenty-fifth Day of February, 2003

JAMES E. ROGAN
*Director of the United States Patent and Trademark Office*